United States Patent
Reda

(10) Patent No.: US 7,663,099 B2
(45) Date of Patent: Feb. 16, 2010

(54) APPARATUS AND METHOD FOR GENERATING AN AMMONIA GAS

(75) Inventor: Ralph J. Reda, Concord, MA (US)

(73) Assignee: Morpho Detection, Inc., Newark, CA (US)

(*) Notice: Subject to any disclaimer, the term of this patent is extended or adjusted under 35 U.S.C. 154(b) by 213 days.

(21) Appl. No.: 11/967,539

(22) Filed: Dec. 31, 2007

(65) Prior Publication Data

US 2009/0166531 A1    Jul. 2, 2009

(51) Int. Cl.
*B01D 59/44* (2006.01)
(52) U.S. Cl. ................................... 250/286
(58) Field of Classification Search ............. 250/286, 250/287, 288
See application file for complete search history.

(56) References Cited

U.S. PATENT DOCUMENTS

| | | | |
|---|---|---|---|
| 5,234,838 A | 8/1993 | Bacon, Jr. | |
| 6,495,824 B1 | 12/2002 | Atkinson | |
| 6,765,198 B2 | 7/2004 | Jenkins et al. | |
| 6,825,460 B2 | 11/2004 | Breach et al. | |
| 6,895,801 B1 | 5/2005 | Fine et al. | |
| 6,946,300 B2 * | 9/2005 | Nguyen et al. | 436/110 |
| 7,129,482 B2 | 10/2006 | Miller et al. | |
| 7,204,125 B2 | 4/2007 | Fine et al. | |
| 7,241,989 B2 | 7/2007 | Miller et al. | |

\* cited by examiner

*Primary Examiner*—Kiet T Nguyen
(74) *Attorney, Agent, or Firm*—Armstrong Teasdale LLP

(57) ABSTRACT

Apparatus and method for generating ammonia gas. In one aspect, a method for generating ammonia gas for use in an ion mobility spectrometry (IMS) system is provided. The method includes inserting a device into a space defined within the IMS system, the device including an ammonia compound. The method also includes activating to decompose and to produce the ammonia gas without producing water vapor. The method also includes emitting the ammonia gas into the IMS system.

20 Claims, 3 Drawing Sheets

APPARATUS AND METHOD FOR GENERATING AN AMMONIA GAS

FIELD OF THE INVENTION

The field of the invention relates generally to generating ammonia gas and, more particularly, to an apparatus and method for generating ammonia gas for use in an ion mobility spectrometry (IMS) system.

BACKGROUND OF THE INVENTION

Since the events of Sep. 11, 2001, the Department of Homeland Security has increased security dramatically in U.S. airports. Such security efforts include screening passengers and carry-on bags and luggage for contraband including narcotics and/or explosive materials.

At least some known security scanning systems employ ion mobility spectrometry to localize and/or identify contraband, such as narcotics and explosives. Many such spectrometers add ammonia gas molecules to a carrier gas to filter a spectrum analyzed by the spectrometer by removing interfering compounds, such as environmental compounds. At least some known spectrometers use ammonia gas generated from the evaporation of liquid anhydrous ammonia. The liquid ammonia must be pressurized to maintain a liquid form at room temperature. The National Fire Protection Association (NFPA) 704 Hazard Rating System considers liquid anhydrous ammonia a Category 3 highly toxic material and, according to the International Air Transport Association, liquid anhydrous ammonia may not be transported on passenger aircraft.

Moreover, at least some known spectrometers use ammonia gas generated from gas permeation devices, such as sealed capsules containing pressurized liquid anhydrous ammonia. Such gas permeation devices emit ammonia gas at a consistent rate through a gas-permeable surface. Such gas permeation devices may be composed of stainless steel tubes, with a permeable membrane at one end of the tube. However, the metal tubes and endcaps are opaque and do not provide a method for visually inspecting the remaining ammonia level. In addition, to be transported, such devices must be able to withstand a pressure of approximately 2,000 pounds per square inch (PSI) without leaking, and require a scrubber cartridge containing ammonia-absorbent material to be packaged with the device. Because such devices must be pressurized, the transportation options are limited.

Other known gas permeation devices may be composed of Teflon permeation tubes containing anhydrous ammonia in a two-phase equilibrium between a gas phase and a liquid phase. At a constant temperature, such devices emit ammonia gas through permeable walls at a constant rate. Such Teflon devices continuously emit ammonia gas at room temperature and must be refrigerated to extend the lifetime of the devices. Such Teflon devices must also be pressurized due to the use of liquid anhydrous ammonia, limiting transportation options.

Alternatively, bottled calibration gases having a mixture of air and a known amount of ammonia gas may be used to provide ammonia gas. However, gas cylinders require regulators and significant storage space. Such gas cylinders may be used in laboratory environments but are not conducive for portable instrument applications. Moreover, static mixtures within the gas cylinders are often unreliable and inaccurate at the concentration levels needed for the demands of IMS technology.

Another method of providing ammonia gas for use in IMS systems includes reacting ammonium salts with a strong base to liberate the ammonia gas. However, such reactions require that the ammonium salts and base are mixed together and heated in order to liberate the ammonia gas. Water is a product of such reactions, and water and/or water vapor interfere with IMS analyses.

The need for pressurized liquid anhydrous ammonia restricts the available methods of transportation of ammonia generation devices. For example, such devices may be required to be shipped via motor vehicle, rail freight, cargo vessel, and/or dedicated cargo aircraft, but may not be shippable using conventional passenger transportation methods. Moreover, the use of alternative sources, such as ammonium carbonate (Chemical Abstract Service Number 506-87-6) or ammonium bicarbonate (CAS Number 1066-33-7) to generate ammonia gas also produces water vapor, which may interfere with the detection and/or analysis abilities of such spectrometers. Further, the use of stainless steel tubes does not allow visual inspection of the remaining lifetime of the device. There is therefore a need for an ammonia generation and delivery device that does not require pressurization and allows visual inspection of the remaining lifetime of the device.

BRIEF DESCRIPTION OF THE INVENTION

In one aspect, a method for generating ammonia gas for use in an ion mobility spectrometry (IMS) system is provided. The method includes inserting a device into a space defined within the IMS system, the device including an ammonia compound. The method also includes activating the ammonia compound to decompose and to produce the ammonia gas without producing water vapor. The method also includes emitting the ammonia gas into the IMS system.

In another aspect, an ammonia gas generation device for use in an ion mobility spectrometry (IMS) system is provided. The ammonia gas generation device includes a gas permeable tube containing an ammonia compound and is sized to be inserted into a space within the IMS system. The device is configured to activate the ammonia compound to decompose into an ammonia gas that does not include water vapor, and emit the ammonia gas into the IMS system.

In another aspect, an ion mobility spectrometry (IMS) system is provided, which includes an ammonia gas generation device including a gas permeable tube containing an ammonia compound. The ammonia gas generation device is sized to be inserted into a space defined by the IMS system and is configured to activate the ammonia compound to begin decomposition of the ammonia compound into an ammonia gas that does not include water vapor. The system also includes an ionization chamber including an ionizing source for ionizing particles. The ammonia gas generation device is further configured to emit the ammonia gas into the ionization chamber. The system also includes a drift tube forming a passage in flow communication with the ionization chamber, a detector for detecting ionized particles exiting the passage, and a processor programmed to determine at least one of the rate of movement of each detected ionized particle and a volume of each detected ionized particle.

BRIEF DESCRIPTION OF THE DRAWINGS

FIG. 1 is a simplified block diagram of an ion mobility spectrometry (IMS) system.

FIG. 2 is a schematic diagram of an ammonia gas generation device that may be used with the ion mobility spectrometry (IMS) system shown in FIG. 1.

FIG. 3 is a schematic diagram of an alternative embodiment of an ammonia gas generation device that may be used with the ion mobility spectrometry (IMS) system shown in FIG. 1.

FIG. 4 is a flowchart illustrating a method of using the gas generation devices shown in FIGS. 2 and 3 to generate an ammonia gas for use in the ion mobility spectrometry (IMS) system shown in FIG. 1.

DETAILED DESCRIPTION OF THE INVENTION

The embodiments described herein provide an apparatus and method for generating an ammonia gas for use in an ion mobility spectrometry (IMS) system that is used for security scanning. In one embodiment, a device containing a predetermined amount of an ammonia compound is inserted into a predefined space within the IMS system. The ammonia compound is activated within the device, causing the ammonia compound to decompose into an ammonia gas that does not contain water vapor. The ammonia gas is then emitted into the IMS system for use in identifying contraband. Moreover, the embodiments described herein provide technical effects such as, but not limited to, generating a dry ammonia gas through decomposition of an ammonia compound, and emitting the ammonia gas into an IMS system for use in identifying a presence of contraband and/or a likely chemical composition of the contraband.

At least one embodiment of the present invention is described below in reference to its application in connection with and operation of a system for inspecting passengers for contraband in their possession. Such contraband may be concealed in, for example, a pocket or between layers of clothing. As used herein, the terms "on a subject" or "near a subject" describe possession of contraband or suspected contraband by the subject. However, it should be apparent to those skilled in the art and guided by the teachings herein provided that the invention is likewise applicable to any suitable system for scanning people including, without limitation, visitors to secured locations and/or employees at sensitive locations. Moreover, the invention is likewise applicable to any system for scanning passengers that are transported by water, land, and/or air.

Figure 1:
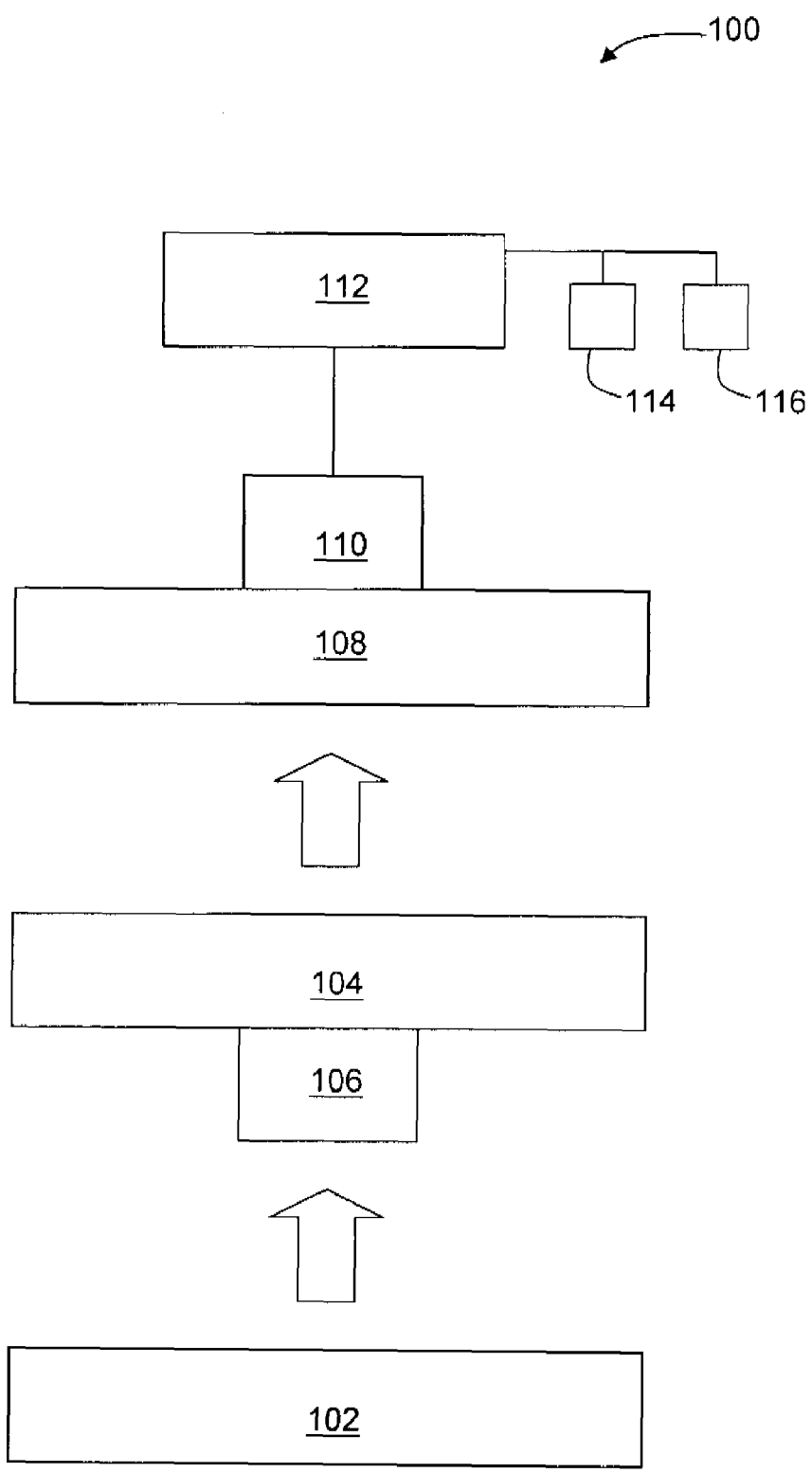
FIGS. 1-4 show exemplary embodiments of the system and method described herein.

FIG. 1 is a simplified block diagram of an ion mobility spectrometry (IMS) system 100 for use in analyzing microscopic particles and vapors naturally emitted by organic substances, such as passengers and/or contraband possessed by passengers, in order to detect and/or identify the contraband. Samples are collected by wiping surfaces of suspected contamination, such as a passenger's skin, or by analyzing concentrated vapors within a sealed container, such as a security portal. IMS system 100 identifies compounds based on an amount of time it takes ionized molecules within IMS system 100 to pass through an electrified field in a tube. This time may be referred to as a "drift time," and is compared to a list of known transit times of a set of compounds, enabling the identification of contraband such as explosives and/or narcotics. IMS system 100 may be used in a handheld inspection device, a desktop inspection device, and/or a freestanding inspection portal.

IMS system 100 includes an ammonia generation device 102 that generates an ammonia gas for use as a dopant in positive-mode ion analysis. The ammonia gas is used to improve the selectivity of IMS system 100. Adding the ammonia gas as a dopant to a carrier gas stream at low concentration removes interfering compounds from the spectrum, facilitating a more accurate analysis by IMS system 100. The ammonia acts as a carrier gas and transports subject gases or vapors into the ion mobility spectrometer. The ammonia gas has a basicity, or proton affinity, which is considerably greater than other known interferant molecules, yet has a sufficiently lower basicity than the molecules of interest. Consequently, the background ion spectrum detected by IMS system 100 will show only ion peaks associated with dopant species.

IMS system 100 also includes an ionization chamber 104 and an ionizing source 106 coupled to ionization chamber 104. A gaseous sample, including the carrier gas having an ammonia gas component, enters ionization chamber 104 where ionizing source 106 emits low-energy beta particles, resulting in ion formation from the gas particles within the gaseous sample. A gating mechanism, such as a shutter grid (not shown), directs ions having a desired polarity into an ion drift region, such as a drift tube 108, which forms a passage in flow communication with ionization chamber 104. In the exemplary embodiment, only positive ions are directed by the shutter grid into drift tube 108 through a first end of drift tube 108. An electric field is applied within drift tube 108, which mobilizes the ions and directs the ions towards an opposite second end, or exit, of drift tube 108. The rate at which the ions move through drift tube 108 is related, such as inversely proportionally related, to the size, or volume, of the ions. A detector 110 is positioned at the exit of drift tube 108. Detector 110 is coupled in signal communication with a processor 112. Detector 110 senses or detects when the ions exit drift tube 108, and generates a signal representative of each ion sensed. Detector 110 then transmits the signal to processor 112. Processor 112 determines a drift time for each ion by determining an amount of time between when the ion entered drift tube 108, signaled to processor 112 by the shutter grid, and when the ion exited drift tube 108, signaled to processor 112 by detector 110. Processor 112 determines an identity of the ionized molecules according to the drift time by comparing the drift time to a database (not shown) of known drift times associated with known substances. Processor 112 then displays the identity of the ionized molecules to an operator using, for example, a display 114 coupled to processor 112. The operator may also manipulate IMS system 100 using an input device 116 coupled to processor 112, such as a keyboard and/or a mouse. Processor 112 may include any programmable system including systems using microcontrollers, reduced instruction set circuits (RISC), application specific integrated circuits (ASIC), programmable logic circuits (PLC), and/or any other circuit or processor capable of executing the functions described herein. The above examples are exemplary only and are thus not intended to limit in any way the definition and/or meaning of the term processor.

Figure 2:
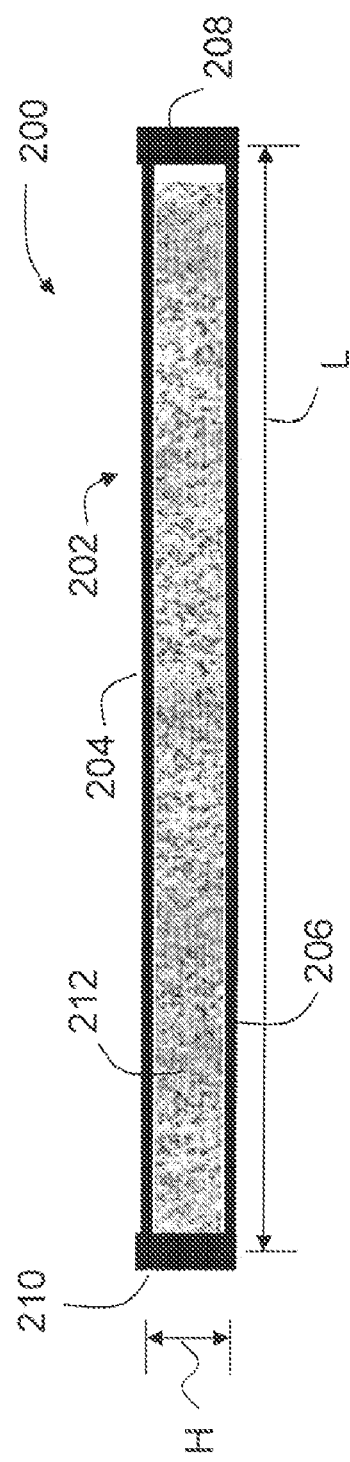

FIG. 2 is a schematic diagram of an exemplary embodiment of an ammonia gas generation device 200 that may be used with ion mobility spectrometry (IMS) system 100 (shown in FIG. 1). In the exemplary embodiment, device 200 defines a gas permeable tube 202 with a first portion, such as a top surface 204, and an opposite second portion, such as bottom surface 206. Device 200 also includes a first end 208 and an opposite second end 210. In some embodiments, first end 208 and second end 210 include sealing components, such as end caps, plugs, or stoppers, that are sized to couple to tube 202 such that an ammonia compound 212 is prevented from leaking or escaping. In the embodiment shown in FIG. 2, top surface 204 is gas permeable and allows ammonia gas to be emitted into IMS system 100 at a known rate, as described below. Device 200 has a length, L, and a height, H. In the embodiment shown in FIG. 2, length, L, measures approximately 100.0 millimeters (mm) and height, H, measures approximately 10.0 mm. However, alternative embodiments of device 200 may include dimensions, such as length, L, and height, H, which vary from those described herein. A predetermined amount of ammonia compound 212 is enclosed within device 200 for use in the generation of ammonia gas. Tube 202 is translucent, such as clear or transparent, to enable an operator of IMS system 100 to determine a remaining amount of ammonia compound 212 within tube 202, thereby determining a remaining lifetime of device 200.

Figure 3:
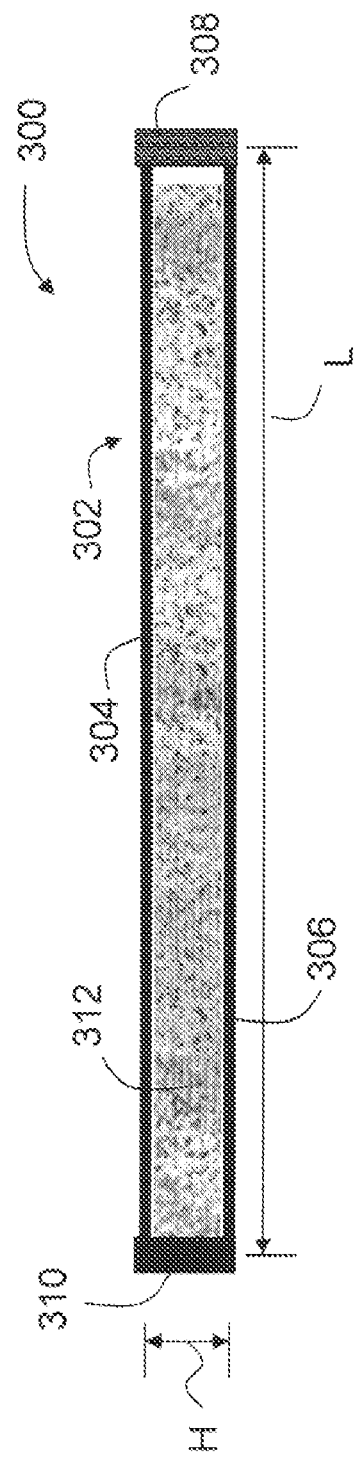

FIG. 3 is a schematic diagram of an exemplary embodiment of an ammonia gas generation device 300 that may be used with ion mobility spectrometry (IMS) system 100 (shown in FIG. 1). In the exemplary embodiment, device 300 defines a tube 302 with a first portion, such as a top surface 304, and an opposite second portion, such as a bottom surface 306. Device 300 also includes a first end 308 and an opposite second end 310. In some embodiments, first end 308 and second end 310 include sealing components, such as end caps, plugs, or stoppers, that are sized to couple to tube 302 such that an ammonia compound 312 is prevented from leaking or escaping. In the embodiment shown in FIG. 3, first end 308 is gas permeable and allows ammonia gas to be emitted into IMS system 100 at a known rate, as described below. In an alternative embodiment, first end 308 and/or second end 310 are gas permeable. Device 300 has a length, L, and a height, H. In the embodiment shown in FIG. 3, length, L, measures approximately 100.0 millimeters (mm) and height, H, measures approximately 10.0 mm. However, alternative embodiments of device 300 may include dimensions, such as length, L, and height, H, which vary from those described herein. A predetermined amount of ammonia compound 312 is enclosed within device 300 for use in the generation of ammonia gas. Tube 302 is translucent, such as clear or transparent, to enable an operator of IMS system 100 to determine a remaining amount of ammonia compound 312 within tube 302, thereby determining a remaining lifetime of device 300.

Figure 4:
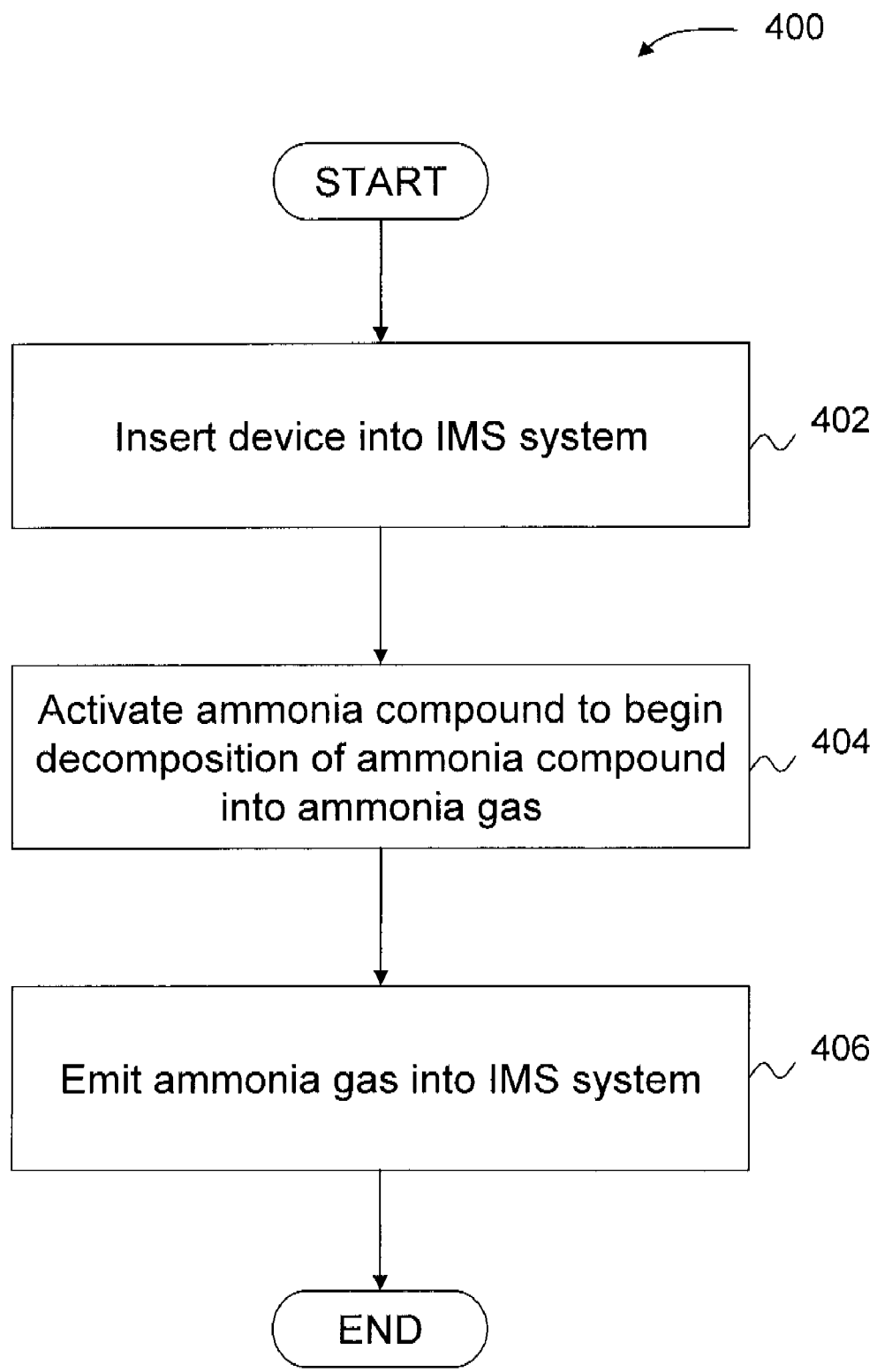

FIG. 4 is a flowchart illustrating an exemplary method 400 of using a gas generation device, such as device 200, shown in FIG. 2, or device 300, shown in FIG. 3 to generate an ammonia gas for use in ion mobility spectrometry (IMS) system 100 (shown in FIG. 1). In the exemplary embodiment, device 200 or device 300 is inserted 402 into a space, or chamber, defined in IMS system 100. The amount of ammonia gas needed for use in IMS system 100 determines whether device 200, having a gas permeable top surface 204 (shown in FIG. 2), or device 300, having a gas permeable first end 308, is used. In addition, the amount of ammonia generated by device 200 or device 300 may be controlled by the surface area of a gas permeable surface, such as top surface 204 or first end 308. Alternatively, the amount of ammonia generated by device 200 or device 300 may be controlled by the permeability of a gas permeable surface, such as top surface 204 or first end 308.

In the exemplary embodiment, ammonia compound 212 within device 200 or ammonia compound 312 within device 300 is activated 404. Activation may be accomplished by exposing device 200 or device 300 to the ambient operating temperature of IMS system 100. Activating ammonia compound 212 or ammonia compound 312 causes a decomposition of ammonia compound 212 or ammonia compound 312 within device 200 or device 300 to begin, producing ammonia gas and carbon dioxide. In the exemplary embodiment, ammonia compound 212 or ammonia compound 312 is ammonium carbamate (CAS Number 1111-78-0, chemical formula $NH_4NH_2CO_2$). In alternative embodiments, a suitable ammonia compound 212 or ammonia compound 312 may be used as long as device 200 and device 300 function as described herein. The use of ammonium carbamate is advantageous for use in IMS system 100 because ammonium carbamate decomposes into ammonia ($NH_3$) and carbon dioxide ($CO_2$) without producing any water vapor. Water molecules in water vapor may degrade the selectivity of IMS systems, such as IMS system 100, because the water molecules are attracted to the ions produced within ionization chamber 104 (shown in FIG. 1), thereby interfering with detection of the ions.

In the exemplary embodiment, 2.0 molecules of ammonia gas are generated for every 1.0 molecule of ammonium carbamate that decomposes. In terms of mass, 0.44 grams of ammonia gas are generated for every 1.0 gram of ammonium carbamate that decomposes. The decomposition of the ammonium carbamate compound 212 or ammonium carbamate compound 312 into ammonia gas depends on temperature and follows the Arrhenius equation, shown as Equation 1 below, such that higher temperatures result in a higher rate of decomposition and, therefore, higher emissions of ammonia gas into IMS system 100. The Arrhenius equation describes the temperature dependence of the rate of a chemical reaction and is shown as:

$$k=Ae^{-E_a/RT} \quad \text{Eq. (1)}$$

Where k is a rate of the chemical reaction, A is a pre-exponential factor, $E_a$ is an activation energy of the reaction, R is a gas constant, and T is temperature.

As the ammonia gas is generated through decomposition of ammonia compound 212 or ammonia compound 312, the ammonia gas and carbon dioxide are emitted 406 into IMS system 100 through a gas permeable surface of device 200 or device 300, such as top surface 204 or first end 308. As ammonia compound 212 or ammonia compound 312 are consumed by decomposing into ammonia gas and carbon dioxide, the amount of ammonia compound 212 or ammonia compound 312 within device 200 or device 300 is reduced. An operator or user of IMS system 100 may determine a remaining amount of ammonia compound 212 or ammonia compound 312 by viewing device 200 or device 300. The translucence, or transparency, of tube 202 or tube 302 therefore facilitates observing a remaining lifetime of device 200 or device 300 and/or ammonia compound 212 or ammonia compound 312.

In summary, in one embodiment, an ammonia gas generation device for use in an ion mobility spectrometry (IMS) system includes a gas permeable tube containing an ammonia compound, such as ammonium carbamate. The device has suitable dimension to be inserted into a space or chamber within the IMS system, and is configured to activate the ammonia compound such that the ammonia compound begins decomposition into the ammonia gas, without also producing water vapor. The ammonia gas is then emitted into the IMS system for use in detecting and/or identifying contraband possessed by a subject under inspection.

In one embodiment, at least a portion of the gas permeable tube is translucent, or transparent, to facilitate determining a remaining lifetime of the ammonia compound by viewing the remaining amount of ammonia compound left in the device. In one embodiment, the gas permeable tube includes a gas permeable portion, such as a first or top surface or wall, through which the ammonia gas is emitted into the IMS system. In an alternative embodiment, the ammonia gas is emitted into the IMS system through a gas permeable end cap, such as a first end cap coupled to the tube.

In addition, the tube includes a gas permeable surface such that the rate of decomposition of the ammonia compound into ammonia gas may be determined by a surface area of the gas permeable surface. In an alternative embodiment, the rate of decomposition of the ammonia compound into ammonia gas may be determined by a permeability of the gas permeable surface.

While the methods and systems described herein have been described in terms of various specific embodiments, those skilled in the art will recognize that the methods and systems described herein may be practiced with modification within the spirit and scope of the appended claims.

What is claimed is:

1. A method for generating ammonia gas for use in an ion mobility spectrometry (IMS) system, said method comprising:
    inserting a device into a space defined within the IMS system, the device including an ammonia compound;
    activating the ammonia compound to decompose and to produce the ammonia gas without producing water vapor; and
    emitting the ammonia gas into the IMS system.

2. A method in accordance with claim 1, determining a remaining lifetime of the ammonia compound by viewing through a translucent tube of the device a remaining amount of the ammonia compound within the device.

3. A method in accordance with claim 1, wherein inserting a device into a space within the IMS system comprises inserting a device that includes ammonium carbonate.

4. A method in accordance with claim 1, further comprising controlling a rate of ammonia gas generation based on a surface area of a gas permeable surface of the device.

5. A method in accordance with claim 1, further comprising controlling a rate of ammonia gas generation based on a permeability of a gas permeable surface of the device.

6. A method in accordance with claim 1, wherein emitting the ammonia gas into the IMS system comprises emitting the gas through a gas permeable surface of the device.

7. A method in accordance with claim 6, wherein emitting the ammonia gas into the IMS system further comprises emitting the ammonia gas through at least one of a gas permeable device wall and a gas permeable device end.

8. An ammonia gas generation device for use in an ion mobility spectrometry (IMS) system, said ammonia gas generation device comprising a gas permeable tube containing an ammonia compound, said ammonia gas generation device sized to be inserted into a space within the IMS system, said ammonia gas generation device configured to:
    activate the ammonia compound to decompose into an ammonia gas that does not include water vapor; and
    emit the ammonia gas into the IMS system.

9. An ammonia gas generation device in accordance with claim 8, wherein said gas permeable tube further comprises a translucent tube that facilitates determining a remaining lifetime of the ammonia compound by viewing a remaining amount of the ammonia compound within said gas permeable tube.

10. An ammonia gas generation device in accordance with claim 8, wherein said gas permeable tube further comprises a gas permeable wall through which the ammonia gas is emitted into the IMS system.

11. An ammonia gas generation device in accordance with claim 8, wherein said gas permeable tube further comprises a gas permeable end cap through which the ammonia gas is emitted into the IMS system.

12. An ammonia gas generation device in accordance with claim 8, wherein said gas permeable tube further comprises a gas permeable surface, a rate of ammonia gas generation determined by a surface area of said gas permeable surface.

13. An ammonia gas generation device in accordance with claim 8, wherein said gas permeable tube further comprises a gas permeable surface, a rate of ammonia gas generation determined by a permeability of said gas permeable surface.

14. An ammonia gas generation device in accordance with claim 8, wherein the ammonia compound comprises ammonium carbonate.

15. An ion mobility spectrometry (IMS) system, comprising:
    an ammonia gas generation device comprising a gas permeable tube containing an ammonia compound, said ammonia gas generation device positioned within a space defined by said IMS system, said ammonia gas generation device configured to activate the ammonia compound to begin decomposition of the ammonia compound into an ammonia gas that does not include water vapor;
    an ionization chamber comprising an ionizing source for ionizing particles, said ammonia gas generation device further configured to emit the ammonia gas into said ionization chamber;
    a drift tube forming a passage in flow communication with said ionization chamber;
    a detector for detecting ionized particles exiting said passage; and
    a processor programmed to determine at least one of a rate of movement of each detected ionized particle and a volume of each detected ionized particle.

16. An ion mobility spectrometry (IMS) system in accordance with claim 15, wherein said gas permeable tube further comprises a translucent tube that facilitates determining a remaining lifetime of the ammonia compound by viewing a remaining amount of the ammonia compound within said gas permeable tube.

17. An ion mobility spectrometry (IMS) system in accordance with claim 15, wherein said gas permeable tube further comprises a gas permeable wall through which the ammonia gas is emitted into said ionization chamber.

18. An ion mobility spectrometry (IMS) system in accordance with claim 15, wherein said gas permeable tube further comprises a gas permeable end cap through which the ammonia gas is emitted into said ionization chamber.

19. An ion mobility spectrometry (IMS) system in accordance with claim 15, wherein said gas permeable tube further comprises a gas permeable surface, a rate of ammonia gas generation is determined by at least one of a surface area of said gas permeable surface and a permeability of said gas permeable surface.

20. An ion mobility spectrometry (IMS) system in accordance with claim 15, wherein the ammonia compound comprises ammonium carbonate.

* * * * *

UNITED STATES PATENT AND TRADEMARK OFFICE
CERTIFICATE OF CORRECTION

| | | |
|---|---|---|
| PATENT NO. | : 7,663,099 B2 | Page 1 of 1 |
| APPLICATION NO. | : 11/967539 | |
| DATED | : February 16, 2010 | |
| INVENTOR(S) | : Reda | |

It is certified that error appears in the above-identified patent and that said Letters Patent is hereby corrected as shown below:

In Claim 3, delete "carbonate" and insert therefor --carbamate--.

In Claim 14, delete "carbonate" and insert therefor --carbamate--.

In Claim 20, delete "carbonate" and insert therefor --carbamate--.

Signed and Sealed this
Eighth Day of March, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,663,099 B2 | Page 1 of 1 |
| APPLICATION NO. | : 11/967539 | |
| DATED | : February 16, 2010 | |
| INVENTOR(S) | : Reda | |

It is certified that error appears in the above-identified patent and that said Letters Patent is hereby corrected as shown below:

In Claim 3, Column 7, line 28, delete "carbonate" and insert therefor --carbamate--.

In Claim 14, Column 8, line 15, delete "carbonate" and insert therefor --carbamate--.

In Claim 20, Column 8, line 59, delete "carbonate" and insert therefor --carbamate--.

This certificate supersedes the Certificate of Correction issued March 8, 2011.

Signed and Sealed this
Twenty-ninth Day of March, 2011

David J. Kappos
*Director of the United States Patent and Trademark Office*